(12) United States Patent
Fech et al.

(10) Patent No.: US 10,589,299 B2
(45) Date of Patent: Mar. 17, 2020

(54) METHOD AND NOZZLE FOR MIXING AND SPRAYING FLUIDS

(71) Applicant: Erbe Elektromedizin GmbH, Tuebingen (DE)

(72) Inventors: Andreas Fech, Tübingen (DE); Klaus Fischer, Nagold (DE); Markus Enderle, Tuebingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 363 days.

(21) Appl. No.: 14/623,035

(22) Filed: Feb. 16, 2015

(65) Prior Publication Data
US 2015/0231653 A1 Aug. 20, 2015

(30) Foreign Application Priority Data

Feb. 17, 2014 (EP) .................................. 14155410

(51) Int. Cl.
*B05B 7/08* (2006.01)
*B05B 7/10* (2006.01)
(Continued)

(52) U.S. Cl.
CPC ...... *B05B 7/0876* (2013.01); *A61B 17/00491* (2013.01); *B01F 5/0413* (2013.01);
(Continued)

(58) Field of Classification Search
CPC ....... B05B 1/3421; B05B 1/3426; B05B 1/26; B05B 7/0807–0861; B05B 7/0876;
(Continued)

(56) References Cited

U.S. PATENT DOCUMENTS 2,136,024 A * 11/1938 Schneider ............. B05B 7/0853
239/306
2,551,699 A * 5/1951 Parks ................... B67D 1/0051
239/404
(Continued)

FOREIGN PATENT DOCUMENTS

GB 2033251 A 5/1980
JP S55-049162 4/1980
(Continued)

OTHER PUBLICATIONS

Office Action in corresponding Korean Application No. 10-2015-0022373, dated Nov. 14, 2016, 6 pages.
(Continued)

*Primary Examiner* — Cody J Lieuwen
(74) *Attorney, Agent, or Firm* — Fitch, Even, Tabin & Flannery LLP

(57) ABSTRACT

The invention relates to a method for mixing at least two fluids using an externally mixing nozzle for medical purposes, which has at least two outlet channels (10, 20) and at least two inlet openings (13, 23) with different or identical cross-sections, wherein two fluids with different volumetric flows and/or different viscosity are sprayed, and wherein the ratio of the cross-sections of the inlet channels (13, 23) and/or the outlet channels (10, 20) corresponds to the ratio of the volumetric flows so that the fluids flow with substantially identical flow speeds through the outlet channels (10, 20) and/or the inlet openings (13, 23). The invention furthermore relates to an externally mixing nozzle, a medical instrument and a medical device for spraying substances, in particular biological material.

12 Claims, 3 Drawing Sheets

(51) Int. Cl.
*A61B 17/00* (2006.01)
*B01F 5/04* (2006.01)
*B01F 5/20* (2006.01)
*A61M 11/08* (2006.01)
*B05B 7/04* (2006.01)

(52) U.S. Cl.
CPC .............. *B01F 5/20* (2013.01); *B05B 7/0846* (2013.01); *B05B 7/10* (2013.01); *A61B 2017/00495* (2013.01); *A61B 2017/00522* (2013.01); *A61M 11/08* (2013.01); *A61M 2205/3379* (2013.01); *B01F 2005/0438* (2013.01); *B01F 2215/0034* (2013.01); *B05B 7/0408* (2013.01)

(58) Field of Classification Search
CPC ......... B05B 7/0884; B05B 7/10; B05B 12/10; B05B 12/1436; B05B 7/0408; A61M 11/008; A61M 2205/3379; A61M 11/08; A61M 5/19; B01F 5/20; B01F 2215/0034; B01F 5/0413; B01F 2005/0438; A61B 17/00491; A61B 2017/00495; A61B 2017/00522
USPC ............... 239/400, 404, 406, 422, 424, 426, 239/543–545, 549, 306, 399, 401–403, 239/405, 468–471, 490–494; 604/68; 606/213, 214; 128/200.14
See application file for complete search history.

(56) References Cited

U.S. PATENT DOCUMENTS

| | | | | |
|---|---|---|---|---|
| 4,284,239 | A | 8/1981 | Ikeuchi | |
| 5,368,563 | A * | 11/1994 | Lonneman | A61B 17/00491 239/404 |
| 5,759,169 | A | 6/1998 | Gerard | |
| 5,759,171 | A | 6/1998 | Coelho et al. | |
| 5,810,885 | A * | 9/1998 | Zinger | A61M 25/0021 604/197 |
| 5,971,298 | A * | 10/1999 | Milian | B05B 7/0081 138/DIG. 8 |
| 6,179,862 | B1 * | 1/2001 | Sawhney | A61B 17/00491 604/197 |
| 6,454,786 | B1 * | 9/2002 | Holm | A61B 17/00491 606/213 |
| 2009/0005731 | A1 * | 1/2009 | Yokoyama | A61B 17/00491 604/83 |
| 2012/0227770 | A1 * | 9/2012 | Kaneko | H01L 21/67051 134/36 |
| 2012/0305669 | A1 * | 12/2012 | Meron | A61B 17/00491 239/428 |
| 2014/0107620 | A1 * | 4/2014 | Fech | A61M 25/0067 604/518 |

FOREIGN PATENT DOCUMENTS

| | | |
|---|---|---|
| JP | H05132503 A | 5/1993 |
| JP | 2000508958 A | 7/2000 |
| JP | 2001502199 A | 2/2001 |
| JP | 2011194304 A | 10/2011 |
| WO | 9001959 A1 | 3/1990 |
| WO | 9733646 A1 | 9/1997 |
| WO | 9813094 A1 | 4/1998 |
| WO | 9917833 A1 | 4/1999 |

OTHER PUBLICATIONS

Office Action and Search Report in corresponding Chinese Application No. 201510075787.2, dated Aug. 9, 2016, 9 pages.
European Search Report for corresponding European application No. EP14155410, dated Jun. 27, 2014, 5 pages.
Office action in corresponding Japanese Application No. 2015-026005, dated Jul. 5, 2016, 9 pages.
Search report in corresponding Japanese Application No. 2015-026005, dated May 25, 2016, 46 pages.

* cited by examiner

METHOD AND NOZZLE FOR MIXING AND SPRAYING FLUIDS

RELATED APPLICATION(S)

This application claims the benefit of European Patent Application No. EP 14155410.5 filed Feb. 17, 2014, the contents of which are incorporated herein by reference as if fully rewritten herein.

TECHNICAL FIELD

The invention relates to a method for mixing at least two fluids by means of an externally mixing nozzle for medical purposes. The invention furthermore relates to an externally mixing nozzle for the supply of substances, in particular biological material as well as a medical instrument and a medical device with such a nozzle.

BACKGROUND

Nozzles for mixing fluids are known, for example, from U.S. Pat. No. 5,368,563 A. In the case of the known nozzle, two vortex chambers are provided into which in each case an outlet channel discharges. Rotational movement of two different fluids is brought about via the vortex chambers before the fluids leave the nozzle via the outlet channels. Due to the vortex applied in advance to the fluids, a rotating spray jet is produced. Here, the two outlet openings of the known nozzle are arranged spaced apart from one another in such a manner that the two rotating fluid cones overlap so that a mixing of the two fluids takes place outside the nozzle.

As a result of the disclosed features of the known nozzle, a uniform mixing of fluids which have a different viscosity and/or are supplied with different volumetric flows cannot be achieved with the desired quality or is not possible in the first place. A further disadvantage of the known nozzle lies in the fact that the fluids in the vortex chambers are exposed to high stresses which is undesirable in the case of the supply of biological material, for example, cells.

SUMMARY

The object of the invention lies in indicating a method for mixing at least two fluids by means of an externally mixing nozzle for medical purposes which enables a uniform mixing of fluids. The object of the invention further lies in indicating an externally mixing nozzle which allows a uniform mixing of fluids and in particular enables a gentle mixing in of a biological material. The object of the invention finally lies in indicating a medical instrument and a medical device with such an externally mixing nozzle.

By one approach, mixing at least two fluids is accomplished by means of an externally mixing nozzle for medical purposes, which nozzle has at least two outlet channels, out of which the fluids can exit out of the nozzle, and at least two inlet openings, through which the fluids in chambers, in particular mixing or vortex chambers, can enter. So that the fluids are mixed outside the nozzle, it may be expedient if at least one of the fluids to be mixed exits in a conical jet out of the nozzle.

The at least two outlet channels and/or the at least two inlet openings can have different or identical cross-sections. In particular, the cross-sections of the inlet openings can be different to one another or identical. The cross-sections of the outlet channels can likewise be different to one another or identical. It is also possible that the cross-section of an outlet channel differs from a cross-section of an inlet opening which is assigned to this outlet channel or these cross-sections are identical. The diameters of the chambers can furthermore be of a different size. In the case of the method according to the invention, a first fluid is conducted via a first supply channel laterally, in particular tangentially, into a first chamber which is fluid-connected to a first outlet channel. A second fluid is conducted via a second supply channel laterally, in particular tangentially, into a second chamber which is fluid-connected to a second outlet channel. The first fluid flows out via the first outlet channel and the second fluid flows out via the second outlet channel so that overlapping fluid cones are formed. The degree of overlapping of the fluid cones can be formed as a function of the intended application. It is thus possible that the overlapping region of both fluid cones is formed from equal proportions of the two fluid cones. It is, however, also possible that the overlapping region is largely only formed by one fluid cone. The fluid cones are determined by the features of the nozzle used in the case of the method as well as the supplied fluids. The first fluid and the second fluid can have a different viscosity and be supplied with different volumetric flows, i.e. in a specific volumetric flow ratio. Moreover, the ratio of the cross-sections of the inlet openings and/or the outlet channels corresponds to the ratio of the volumetric flows. For example, the first fluid and the second fluid can flow with substantially identical flow speeds through the outlet channels and/or the inlet openings. In addition, in particular applications, the chambers can have different diameters. As a result of a correspondingly formed nozzle, it can be ensured that the formation of fluid cones with a sufficiently large opening angle comes about despite different volumetric flows of the first fluid and of the second fluid. This can result in fluid cone regions which are of approximately equal size and which overlap.

It is achieved with the method according to the invention that a uniform mixing of the different fluids is produced in the overlapping fluid cones. Since the flow speeds of the two fluids are adjusted to one another despite their different viscosity or volumetric flows, a good and constant mixing of the fluids is achieved. In this case, the mixing is carried out outside the nozzle so that the risk of nozzle blocking is avoided. The fluids are preferably guided entirely separately from one another within the nozzle. In concrete terms, the cross-linking reaction or mixing of the fluids can be carried out exclusively outside the nozzle.

The nozzle used for the method according to the invention is preferably specially adapted to the properties of two selected fluids. A correspondingly adapted nozzle can thus be provided for each desired fluid combination. The nozzles differ, for example, by the cross-sections of the outlet channels and/or the inlet openings into the chambers, and/or the chamber diameters. As a result of these geometric variables, it is possible to selectively set the flow speeds for predetermined fluids. The externally mixing nozzle can have both two outlet channels with different cross-sections and also two inlet openings with different cross-sections and/or different chamber diameters. It is also possible that the cross-sections of the outlet channels and/or the inlet openings into the chambers are identical. The adjustment of the flow speeds can then be carried out, for example, via a control unit which influences the fluid pressure and/or the volumetric flows of the fluids. In other words, in one preferred configuration of the method according to the invention, it is provided that the supply of the first fluid to the first chamber and/or the supply of the second fluid to the second chamber is controlled.

In this context, reference is made to the fact that the diameter of the chamber relates to the dimension of the chamber in a plane perpendicular to the central axis of the chamber. In the case of the invention, the chamber can in particular take on the function of exerting a vortex on the fluids flowing in via the inlet openings. To this end, the chamber preferably has a round, in particular circular cross-section. The diameter of the round chamber cross-section is referred to as the chamber diameter in the context of the present application.

In a further configuration of the method according to the invention, a third fluid can be conducted through a third supply channel into the second chamber and mixed with the second fluid. The third fluid can therefore already be mixed with the second fluid prior to exiting out of the outlet opening. It is preferably provided that the second fluid and the third fluid do not enter into any or only enter into a minor cross-linking reaction with one another. However, the first fluid can have a cross-linking function so that cross-linking is carried out by mixing the first fluid with the mixture of the second and third fluid outside the nozzle. Cross-linking of all the fluids is preferably carried outside the nozzle, for example, firstly by adding the first fluid to the mixture of the second and third fluid.

In order to reduce the stress to which the fluids are exposed, for example, to reduce shear forces on entry of the third fluid into the second chamber, it can advantageously be provided that the third fluid flows in coaxially into the second chamber. In particular, the third fluid can flow in coaxially with respect to the second chamber into the second chamber, wherein the second chamber is connected coaxially to the second outlet channel. As a result, the third fluid can flow through the second chamber coaxially with respect to the second outlet channel. It is thus largely avoided that the third fluid in the second chamber is exposed to a vortex and/or increased pressure, which would result in increased stress, in particular shear forces or pressure. The influence of shear forces and/or pressure on the third fluid is minimised so that a particularly gentle supply or mixing in of the third fluid is carried out. The third fluid can contain, for example, a biological material, in particular cells which have a high sensitivity in terms of stress. The biological material is protected by the coaxial supply of the third fluid.

In one alternative variant of the method according to the invention, a third fluid can be conducted via a third outlet channel into the overlapping fluid cones of the first fluid and of the second fluid. In this variant, the third outlet channel is preferably positioned between the first outlet channel and the second outlet channel so that the third fluid is conducted into the mixing or overlapping zone of the fluid cones of the first fluid and of the second fluid. In this manner, the third fluid is brought into connection with the first fluid and the second fluid outside the nozzle so that mixing of all three fluids is carried out entirely outside the nozzle. This avoids a blocking of individual outlet channels or other components of the nozzle. The combining of the fluids outside the nozzle furthermore brings about particularly gentle mixing of these fluids.

A further alternative embodiment of the method according to the invention provides that the third fluid is introduced directly, in particular laterally, into the second outlet channel. The third fluid is sucked in by the flow of the second fluid in the second outlet channel (Venturi principle) and thus arrives at the second outlet channel substantially without compressive stress, wherein at least partially a mixing of the third fluid with the second fluid takes place in the outlet channel. The third fluid is therefore mixed in with the second fluid immediately before exiting from the nozzle, as a result of which the risk of nozzle blocking is reduced. At the same time, a desired mixing of the third fluid with the second fluid is achieved.

In a further aspect, an externally mixing nozzle for the supply of substances, in particular biological material, includes a first outlet channel and a second outlet channel. The first outlet channel and the second outlet channel are arranged spaced apart from one another so that fluid cones exiting from the first and second outlet channels for mixing of fluids at least partially overlap. The first outlet channel is fluid-connected to a first chamber. The second outlet channel is fluid-connected to a second chamber. Moreover, a first supply channel discharges laterally, in particular tangentially, into the first chamber. A second supply channel discharges laterally, in particular tangentially, into the second chamber. According to the invention, at least one third supply channel is provided which discharges coaxially into the second chamber or directly into the second outlet channel or a third outlet channel.

The nozzle according to aspects of the invention enables the supply and mixing of at least three fluids, wherein the mixing of at least two fluids is carried out entirely outside the nozzle. A sticking or blocking of the nozzle is thus efficiently avoided.

The third supply channel can discharge in particular laterally into the second outlet channel. In other words, the third fluid guided in the third supply channel can be mixed in perpendicular to the flow direction of the second fluid which is guided in the second outlet channel. This type of mixing in is particularly effective and simultaneously gentle for substances, in particular biological material which may potentially be contained in the third fluid.

In one preferred variant of the nozzle according to the invention, the third outlet channel is arranged between the first and the second outlet channel so that a fluid exiting from the third outlet channel, in particular the third fluid, is conducted into the overlapping fluid cones. In this variant, the mixing of the at least three fluids is carried out entirely outside the nozzle, which reliably avoids nozzle blocking. As a result of the central arrangement of the third outlet channel between the first and the second outlet channel, the stress on the third fluid exiting from the third outlet channel e.g. as a result of shear forces is reduced.

It can also be provided that the third supply channel is arranged coaxially with respect to the second outlet channel. The third fluid guided in the third supply channel thus arrives coaxially or centrally into the second chamber and can be mixed gently there with a second fluid which flows via the second supply channel into the second chamber. As a result of the lateral discharge of the second supply channel, a vortex arises in the second chamber, which vortex leads to turbulence so that the third fluid, which flows in via the coaxially arranged third supply channel, is well mixed with the second fluid. The coaxial arrangement of the third supply channel simultaneously brings about protection of the third fluid, in particular in terms of occurring stress, in particular shear forces and/or pressure.

In order to achieve an adjustment of the flow speeds of the fluids exiting from the outlet channels and thus an equalisation of the spray cones in terms of the speed components (axial, radial) for optimum homogeneous distribution of the fluids and as large as possible overlapping of the spray cones, it can preferably be provided that the first chamber and the second chamber are connected in each case to the first or second supply channel via an inlet opening, wherein the inlet opening of the first and the inlet opening of the second chamber have different cross-sectional surfaces. The cross-sectional surfaces of the inlet openings of the first chamber or the second chamber can differ in terms of their geometric form and/or their size. The cross-sectional surfaces are preferably of a different size, wherein the size difference between the cross-sectional surfaces is adapted such that the flow speeds of the fluids flowing into the chamber are equalised.

In still another aspect, at least the first outlet channel and the second outlet channel, in particular all the outlet channels, have longitudinal axes aligned parallel or at an angle to one another. A parallel alignment of the longitudinal axes of the outlet channels facilitates the manufacture of the nozzle according to the invention. An enlargement of the overlapping region of the fluid cones is achieved by an angular alignment of the longitudinal axes of the outlet channels. This supports the mixing of the fluids and thus improves the mixing function of the nozzle.

It can furthermore be provided in the case of one preferred exemplary embodiment of the nozzle according to the invention that the second outlet channel has a bottleneck. The third supply channel can discharge into the second outlet channel in particular in the region of the bottleneck. The third supply channel preferably discharges laterally in the region of the bottleneck into the second outlet channel. The bottleneck can substantially form a tapering so that the outlet channel itself is formed in the manner of a Venturi nozzle. The outlet channel thus has different or varying cross-sectional diameters, wherein the cross-section of the outlet channel is preferably circular. Reference is made to the fact that not only the second outlet channel, rather also the first outlet channel and/or the third outlet channel can be formed in the manner of a Venturi nozzle, i.e. can substantially have a bottleneck. The bottleneck forms the smallest cross-sectional diameter of the respective outlet channel. In the case of the comparison of the cross-sectional dimensions of the inlet openings and the outlet channels, the smallest cross-sectional diameter in the region of the bottleneck is called on in terms of the outlet channels which are formed in the manner of a Venturi nozzle. The smallest cross-sectional diameter can be determined, for example, with the help of a measuring cylinder which is guided through the outlet channel. The diameter of the maximum largest measuring cylinder which can be guided through the outlet channel corresponds to the cross-sectional diameter of the outlet channel at the bottleneck or at the smallest cross-sectional diameter.

The flow speed of the fluid flowing through the outlet channel is at its highest in the region of the bottleneck so that, in accordance with the Venturi principle, a vacuum is generated in the supply channel which discharges in the region of the bottleneck into the outlet channel. In this manner, the fluid introduced laterally via the supply channel into the outlet channel can be drawn in with the help of the fluid flowing in the outlet channel, as a result of which pressure stresses on the incoming fluid are avoided.

A subordinate aspect of the invention relates to a medical instrument with a previously described externally mixing nozzle, wherein the instrument can be connected to a medical device with an open-loop or closed-loop control unit for setting the fluid supply.

Moreover, a medical device which is connected to a previously described externally mixing nozzle and/or such an instrument is described in the context of the invention, wherein the medical device has an open-loop and/or closed-loop control unit. The open-loop and/or closed-loop control unit is configured for setting the fluid supply so that, in the case of different volumetric flows and/or different viscosity of the fluids, these flow with substantially identical flow speeds through the outlet channels and/or the inlet openings.

Moreover, a medical device, which is connected to an externally mixing nozzle and/or a previously described instrument, can have an open-loop or closed-loop control unit which is configured for setting the fluid supply in such a manner that the different fluids can be supplied independently of one another, in any desired sequence, for example, at intervals. It is furthermore possible that a medical device has an open-loop or closed-loop control unit which is adapted for setting the fluid supply in such a manner that the flow speeds of the fluids with different volumetric flows and/or different viscosity are equalised to one another and the different fluids can be supplied independently of one another in any desired sequence. As a result, it can be achieved that, for example, the first fluid exits from the first outlet channel out of the nozzle, is sprayed onto a target object, at a time interval from this the second fluid exits from the second outlet channel out of the nozzle and the mixing or cross-linking of the two fluids is first carried out on the target object, for example, a tissue, in particular a biological tissue.

The invention will be explained in greater detail below on the basis of exemplary embodiments with reference to the enclosed schematic drawings. In these drawings:

DETAILED DESCRIPTION

Figure 1:
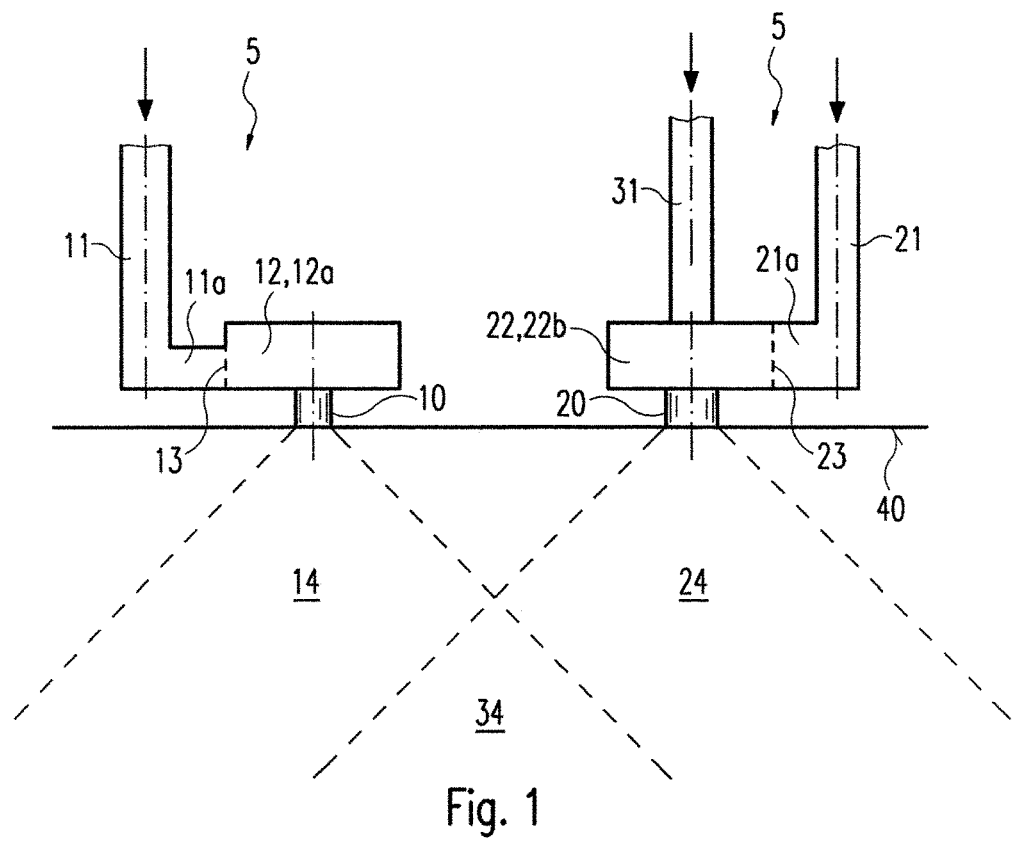
FIG. 1: shows a cross-sectional view through an externally mixing nozzle according to the invention according to a preferred exemplary embodiment, wherein the third supply channel discharges coaxially into the second chamber.

FIG. 1 shows in cross-section an externally mixing nozzle with two different channel systems 5. The nozzle has two outlet channels 10, 20. Outlet channels 10, 20 terminate in an end surface 40 which delimits the nozzle. Both outlet channels 10, 20 form a first outlet channel 10 and a second outlet channel 20. The first outlet channel 10 and the second outlet channel 20 are arranged spaced apart from one another. In the case of the exemplary embodiment shown, it is clearly visible that outlet channels 10, 20 have different cross-sections, in particular cross-sectional diameters. Outlet channels 10, 20 are preferably formed in a circular cylinder form, wherein second outlet channel 20 has a larger cross-sectional diameter than first outlet channel 10.

First outlet channel 10 connects end surface 40 to a chamber 12 which is formed in particular as vortex chamber 12a. Vortex chamber 12a brings about turbulence of the supplied first fluid so that a conical fluid jet is generated when the fluid exits via first outlet channel 10. Fluid cone 14 of the first fluid is represented by dashed lines in the figures.

In order to bring about a rotational movement of the first fluid in vortex chamber 12a, a first supply channel 11 discharges laterally into vortex chamber 12a. In particular, first supply channel 11 can discharge tangentially into first vortex chamber 12a. In other words, first supply channel 11 can have an internal wall which seamlessly or continuously or without a shoulder forms a transition to an internal wall of first vortex chamber 12a.

First supply channel 11 runs substantially perpendicular to end surface 40 through the nozzle and has an angled end portion 11a which runs substantially parallel to end surface 40 through the nozzle and discharges into first chamber 12, in particular first vortex chamber 12a. First supply channel 11 has a first inlet opening 13 in the discharge region between first supply channel 11, in particular its end portion 11a, and first vortex chamber 12a. First inlet opening 13 has a height which is smaller than the height of vortex chamber 12a. The cross-section of first inlet opening 13 can be selected as a function of the viscosity or of the volumetric flow of the supplied first fluid. For example, first inlet opening 13 can have a height which corresponds to the height of vortex chamber 12a.

Second outlet channel 20 connects end surface 40 to a second chamber 22 which is formed in the case of the exemplary embodiment according to FIG. 1 as mixing chamber 22b. In a similar manner to first chamber 12, a second supply channel 21 discharges into second chamber 22. Second supply channel 21 runs substantially parallel to first supply channel 11, i.e. perpendicular to end surface 40, and has an angled end portion 21a which discharges into mixing chamber 22b. Angled end portion 21a of second supply channel 21 discharges in particular via a second inlet opening 23 into second chamber 22 or mixing chamber 22b. In the exemplary embodiments represented here according to FIGS. 1 and 2, second inlet opening 23 has a height which corresponds to the height of mixing chamber 22b or generally second chamber 22. A different dimensioning, in particular in terms of the cross-sectional surface, of second inlet opening 23 is possible and is selected by the person skilled in the art as a function of the volumetric flow and the viscosity of the supplied second fluid.

In the case of the exemplary embodiment according to FIG. 1, it is apparent that second inlet opening 23 has a larger cross-section than first inlet opening 13. It is assumed here that only the heights of the two inlet openings differ. The other parameters which determine the cross-sectional surface of the two inlet openings are identical. In principle, the ratio between inlet openings 13, 23 can be selected to be different or identical in order to set the flow speed of the fluids when exiting out of outlet channels 10, 20 and/or when passing through inlet openings 13, 23, in particular equalise them. Not only the height of inlet openings 13, 23, rather also the width of inlet openings 13, 23, i.e. the respective cross-sectional surface, can be varied here. In general, inlet openings 13, 23 can differ from one another both in terms of their geometric form and in terms of their dimensions.

The nozzle furthermore has a third supply channel 31 which extends substantially parallel to first and second supply channel 11, 21, i.e. perpendicular to end surface 40. Third supply channel 31 serves to supply a third fluid. Third supply channel 31 discharges in the case of the exemplary embodiment according to FIG. 1 directly into second chamber 22 or mixing chamber 22b. Second chamber 22 forms a mixing chamber since both the second fluid and also the third fluid are conducted into second chamber 22 and mixed therein. Third supply channel 31 preferably discharges coaxially with respect second chamber 22 into second chamber 22. In particular, in the case of the exemplary embodiment according to FIG. 1, third supply channel 31, second chamber 22 or mixing chamber 22b and second outlet channel 20 are arranged coaxially with respect to one another. It is achieved as a result that the third fluid is guided substantially without deflection through the nozzle and leaves the nozzle via second outlet channel 20. A mixing of the third fluid with the second fluid simultaneously takes place in mixing chamber 22b since vortexing of the second fluid in mixing chamber 22 is brought about. As a result, it is achieved that second supply channel 21 discharges laterally into mixing chamber 22b. In particular, second supply channel 21 discharges tangentially into mixing chamber 22b. In an analogous manner to first supply channel 11, second supply channel 21 also has an internal surface which forms a flush, i.e. shoulder-free, transition to an internal surface of mixing chamber 22b.

The fluid mixture generated in mixing chamber 22b of the second fluid and the third fluid exits out of second outlet channel 20 as second fluid cone 24.

In general, first chamber 12 and second chamber 22 have the function of bringing about vortexing of the fluid to be sprayed, from which there arises a conical spray jet when the fluids exit out of outlet channels 10, 20. In this manner, two fluid cones 14, 24 are produced which are formed directly after end surface 40. Outlet channels 10, 20 are preferably arranged spaced apart from one another in such a manner that fluid cones 14, 24 overlap and form an overlapping region 34, wherein overlapping region 34 is arranged spaced apart from end surface 40. The mixing of the fluids from fluid cones 14, 24 is carried out in overlapping region 34. As a result of overlapping region 34 arranged at a distance from end surface 40 of the nozzle, it is ensured that fluids, which are mixed in this overlapping region 34, do not block the nozzle, in particular outlet channels 10 and 20 and vortex or mixing chambers 12, 22.

In order to improve the mixing of the fluids outside the nozzle, it can be provided that outlet channels 10, 20, in particular first outlet channel 10 and second outlet channel 20, are arranged at an angle to one another. The longitudinal axes of first outlet channel 10 and of second outlet channel 20 can therefore converge with one another, wherein the point of intersection of the longitudinal axes is arranged outside the nozzle. An enlarged overlapping region 34 is produced from this. In the case of the represented exemplary embodiments, outlet channels 10, 20 are aligned parallel to one another, which has advantages in the manufacture of the nozzle.

Figure 2:
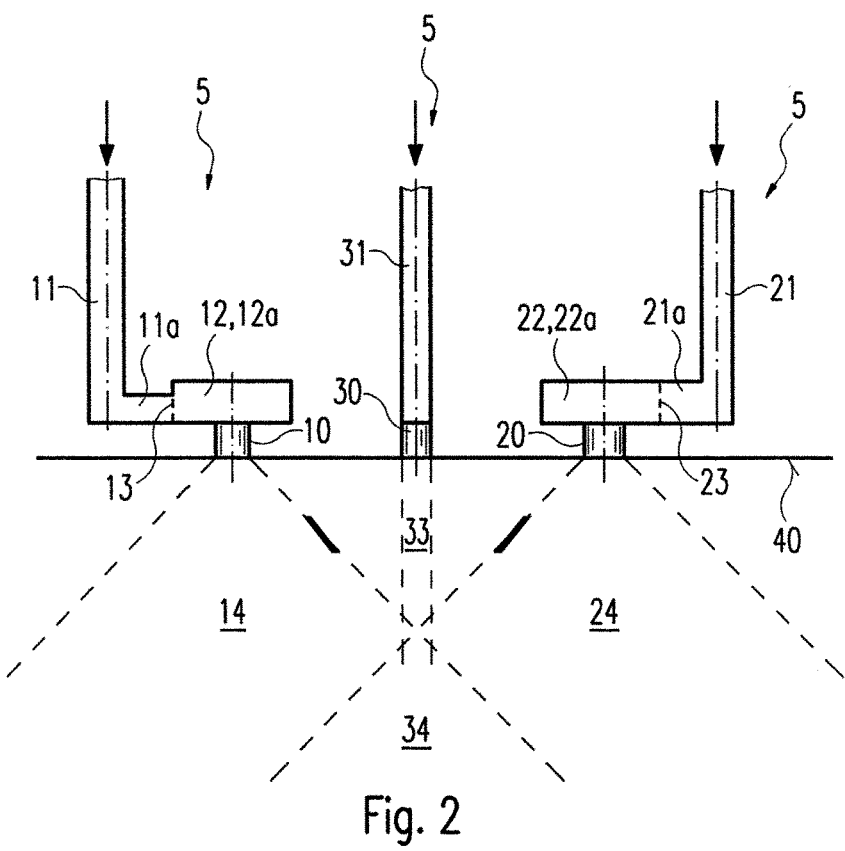
FIG. 2: shows a cross-sectional view of an externally mixing nozzle according to the invention according to a further preferred exemplary embodiment, wherein the third supply channel discharges in a third outlet channel.

FIG. 2 shows a further exemplary embodiment of the nozzle according to the invention with three different channel systems 5, wherein the fluid guide for the first fluid (represented on the left in FIG. 2) is formed to be substantially identical to the nozzle according to FIG. 1. In other words, the nozzle according to FIG. 2 has a first outlet channel 10 which is aligned coaxially with respect to a first chamber 12, in particular a vortex chamber 12a. First outlet channel 10 connects first chamber 12 to an end surface 40 of the nozzle. A first supply channel 11, which has an end portion 11a, discharges laterally into first chamber 12 or first vortex chamber 12a. End portion 11a comprises a first inlet opening 13 in the transition region to first vortex chamber 12a. As in the case of the exemplary embodiment according to FIG. 1, a rotational movement of the first fluid in first vortex chamber 12a is brought about in order to generate a fluid cone 14 when the first fluid exits out of first outlet channel 10.

The second fluid is also guided via a fluid guide to end surface 40 which substantially corresponds to the fluid guide according to FIG. 1. In the case of the nozzle according to FIG. 2, a second outlet channel 20 is provided which is arranged coaxially with respect to a second chamber 22 and second chamber 22 is fluid-connected to end surface 40. A second supply channel 21 discharges into second chamber 22 via an angled end portion 21a and a second inlet opening 23. Second supply channel 21 discharges laterally, in particular tangentially, into second chamber 22. In contrast to the exemplary embodiment according to FIG. 1, second chamber 22 in the case of the exemplary embodiment according to FIG. 2 is formed as second vortex chamber 22a. No fluid mixing takes place in second vortex chamber 22a. Chambers 12, 22 can have different or identical diameters. Only rotational movement of the second fluid is brought about in second vortex chamber 22a in order to generate a fluid cone 24 when the second fluid exits out of second outlet channel 20.

In the case of the exemplary embodiment according to FIG. 2, it is also apparent that first outlet channel 10 and second outlet channel 20 have different cross-sections. In any case, first inlet opening 13 and second inlet opening 23 have different cross-sections. This is, as explained above, variable in order to match the volumetric flows or the viscosity of the different fluids in particular of the first fluid and of the second fluid. For example, by setting a corresponding ratio between the cross-sections of outlet channels 10, 20 and the cross-sections of inlet openings 13, 23, optimised flow speeds, in one particular application, identical flow speeds, are set during entry of the first fluid and of the second fluid into vortex chamber 12a, 22a and/or during exiting of the first fluid and of the second fluid out of outlet channels 10, 20. An optimised flow speed of the first fluid and of the second fluid ensures an optimum overlapping region in the case of minimal (as low as possible) mechanical stress of the materials to be applied.

In the case of the exemplary embodiment according to FIG. 2, a third supply channel 31 is also provided which extends parallel to first supply channel 11 and second supply channel 21. Third supply channel 31 discharges directly into a third outlet channel 30 which is arranged between first outlet channel 10 and second outlet channel 20. Third supply channel 31 and third outlet channel 30 are aligned coaxially with respect to one another so that the third fluid exits out of the nozzle without deflection. The third fluid preferably exits out of third outlet channel 30 as an e.g. low-turbulence jet 33 which flows directly into overlapping region 34. The mixing of all three fluids is thus first carried out in overlapping region 34, i.e. outside the nozzle. Jet 33, which exits out of outlet channel 30, can be a coherent, continuous exit of fluid or an intermittent exit of fluid in the form of drops.

Figure 3:
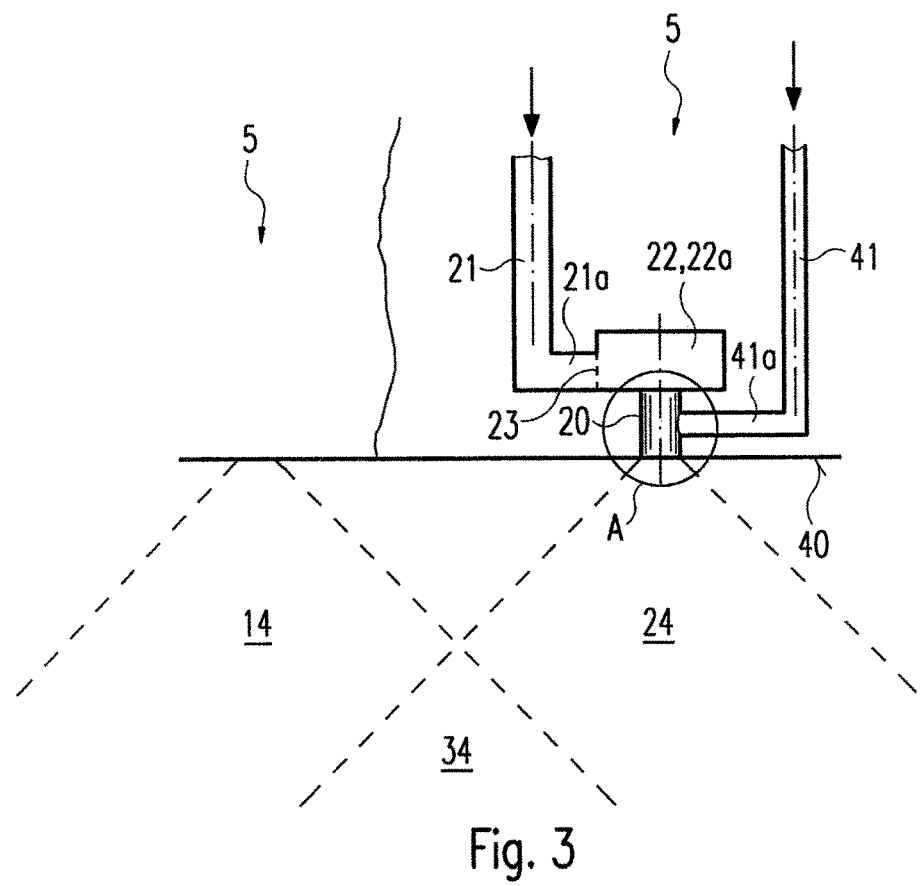
FIG. 3: shows a cross-sectional view of an externally mixing nozzle according to the invention according to a further preferred exemplary embodiment, wherein the third supply channel discharges laterally into the second outlet channel.

A further exemplary embodiment of a nozzle is shown in FIG. 3. For reasons of clarity, a representation of the fluid guide of channel system 5 for the first fluid has been omitted. Only fluid cone 14 of the first fluid is shown in FIG. 3 by dashed lines. The unrepresented part of the nozzle according to FIG. 3 substantially corresponds to the corresponding part in FIGS. 1 and 2. In other words, the nozzle has a first outlet channel 10 which connects first chamber 12, in particular first vortex chamber 12a, to end surface 40. First supply channel 11 discharges laterally into vortex chamber 12a via first inlet opening 13.

The nozzle according to FIG. 3 furthermore has a further channel system 5 with a second outlet channel 20 which terminates at end surface 40. Second outlet channel 20 originates from a second chamber 22 which is configured as a second vortex chamber 22a. Second vortex chamber 22a is arranged coaxially with respect to second outlet channel 20. A second supply channel 21 discharges laterally into second vortex chamber 22a via a second end portion 21a which forms a transition to second vortex chamber 22a in the region of a second inlet opening 23. Second supply channel 21 preferably discharges tangentially into second vortex chamber 22a. Apart from angled end portion 21a, second supply channel 21 runs perpendicular to end surface 40.

A third supply channel 41, which is connected via an angled end portion 41a laterally to second outlet channel 20, also extends perpendicular to end surface 40. End portion 41a of third supply channel 41 preferably extends parallel to end surface 40 or perpendicular to second outlet channel 20.

In the case of the exemplary embodiment according to FIG. 3, it is apparent that second inlet opening 23 has a height which is smaller than the height of second vortex chamber 22a. In general, the cross-section of second inlet opening 23 can be adapted to the viscosity or the volumetric flow of the second fluid in order, when the second fluid exits out of the nozzle, to set a flow speed of the second fluid or the fluid mixture of the second and third fluid, which flow speed is adapted to the flow speed of the first fluid flowing out of first outlet channel 10 (not represented in FIG. 3). As a result of fluid cones 14, 24 generated by means of vortex chambers 12a, 22a, an overlapping region 34 is produced in which the fluids are mixed with one another. In the case of the exemplary embodiment according to FIG. 3, a first mixing of the second fluid with the third fluid is already carried out in second outlet channel 20. It also applies here as in the case of the exemplary embodiments described above that overlapping region 34 is arranged spaced apart from the nozzle or its end surface 40.

Figure 3A:
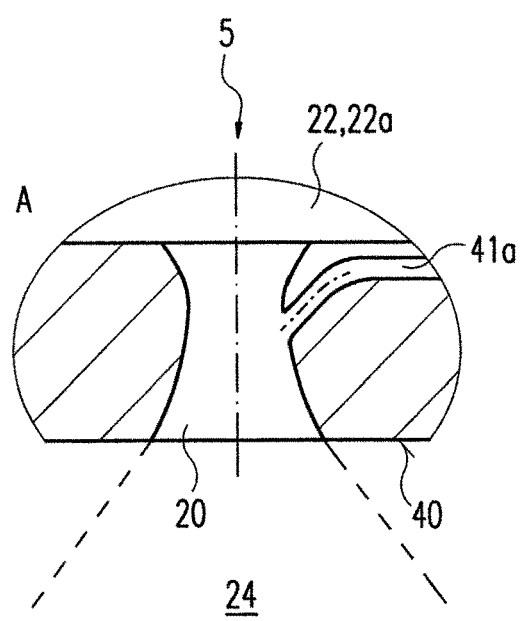
FIG. 3a: shows, in an enlarged representation, a preferred configuration of an outlet channel of an externally mixing nozzle according to the invention according to FIG. 3.

A further embodiment of the nozzle is represented in FIG. 3a. The configuration of outlet channel 20a and of end portion 41a of third supply channel 41 is represented in the cut-out represented in an enlarged form. In this exemplary embodiment, outlet channel 20a is, in contrast to the exemplary embodiments described above, not embodied to be cylindrical with a constant diameter, rather is formed in the manner of a Venturi nozzle. This means that the cross-section of outlet channel 20a has a varying diameter between its proximal and its distal end. In concrete terms, it is provided that outlet channel 20a has a bottleneck 15 between chamber 22 and end surface 40. It is furthermore advantageously provided that end portion 41a is arranged at an angle of less than 90° with respect to the longitudinal axis of outlet channel 20a. The discharge point of end portion 41a is preferably arranged at the narrowest point, i.e. in the region of bottleneck 15, of outlet channel 20a. This arrangement facilitates the generation of a vacuum in end portion 41a and thus a suction effect on the third fluid. The arrangement of end portion 41a at an angle of less than 90° also facilitates a gentle transfer of the third fluid into second outlet channel 20a. For improved distribution and mixing of the second and third fluid in second outlet channel 20a, third supply channel 41 and end portion 41a can be present in a multiple design e.g. in triplicate (not shown in FIG. 3a). At least end portions 41a can be arranged symmetrically around outlet channel 20.

A nozzle according to the invention can have any possible combination of the channel systems described above for the supply of fluids. Nozzles with at least two channel systems 5 or, for example, with four or several channel systems 5 are thus possible. Irrespective of the type and/or number of channel systems used, at least two fluids are mixed in the case of a nozzle according to the invention in an overlapping region 34 which is arranged outside the nozzle.

Figure 4:
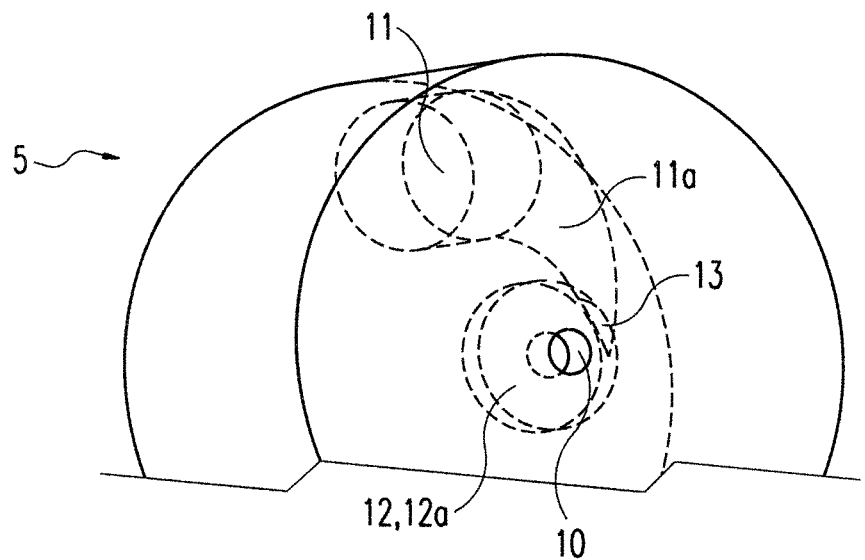
FIG. 4: shows a perspective view of an advantageous channel system of an externally mixing nozzle according to the invention in a one-piece design.

In a further exemplary embodiment, the nozzle can be formed from one or several channel systems 5 which are embodied in each case in one piece. It is also possible that the entire nozzle is formed in one piece. FIG. 4 shows a one-piece embodiment of a channel system 5, wherein for reasons of clarity the representation of other channel systems 5 has been omitted. Outlet channels 10, 20, 30, chambers 12, 22, inlet openings 13, 23 and supply channels 11, 21, 31 (represented by a dashed line in FIG. 4) are embodied integrally in one component. In the case of this embodiment of the nozzle, the fluid preferably flows through edge-free deflections into the mixing chamber. This means that radially outwardly offset supply channels 11, 21, 31 are formed to be tubular. In contrast to the exemplary embodiments described above, in the case of which supply channels 11, 21 are formed by surface portions joined together, in particular their deflection regions, in the case of the nozzle embodied in one piece, these deflection regions are formed by cylindrical, edge-free line portions. This enables a gradual deflection of the fluid to be supplied even in the case of a change in the direction of flow of up to 90 degrees. As a result, the fluid to be supplied can be supplied in a gentle manner to chambers 12, 22. The configuration of supply channels 11, 21 enables a continuous, gradual deflection of the direction of flow of the fluids flowing through these supply channels 11, 13 from the proximal end of the nozzle up to entry into chambers 12, 22. Although the direction of flow proceeding from the distal end of supply channels 40, 50, 51 up to the mixing chamber changes by up to 90 degrees, supply channels 11, 12 are preferably formed infinitely variably or with continuously infinitely variable curves. In particular, supply channels 11, 12 have on this entire section no points which generate an abrupt deflection of the direction of flow.

Supply channels 11, 12 which are substantially infinitely variably formed or are fitted with continuous curves are particularly suitable for the supply of biological material, in particular cells. In the case of the exemplary embodiment according to FIG. 4, first supply channel 11 discharges via an end portion 11a into first chamber 12 or first vortex chamber 12a. End portion 11a of first supply channel 11 has continuously curved lateral surfaces so that fluid flowing through first supply channel 11 is guided gently in a continuous curve to first inlet opening 13. The side walls of end portion 11a of first supply channel 11 forms a substantially infinitely variable transition to the side walls of first chamber 12 so that a vortex motion of the fluid flowing into first chamber 12 is brought about immediately. Such a configuration of first supply channel 11 with a curved end portion 11a and a continuous transfer into chamber 12 is indeed particularly suitable for the supply of biological cells or fluids which contain biological cells. Channel system 5 according to FIG. 4 is, however, also suitable for the supply of other materials or fluids.

The variants described above of the nozzle according to the invention can be coupled in each case to an open-loop or closed-loop control unit in order to set the flow speeds of the fluids on exiting out of the nozzle, in particular as a function of the individual volumetric flows and/or the individual viscosity of the fluids. The open-loop or closed-loop control unit is directed at setting a uniform flow speed for all the fluids. The open-loop or closed-loop control unit can furthermore bring about a spraying of the fluids, wherein the different fluids exit out of the nozzle independently of one another and/or in any desired sequence. In other words, the nozzle can be actuated in such a manner that fluids exit out of outlet channels 10, 20, 30 sequentially or simultaneously.

Figure 5:
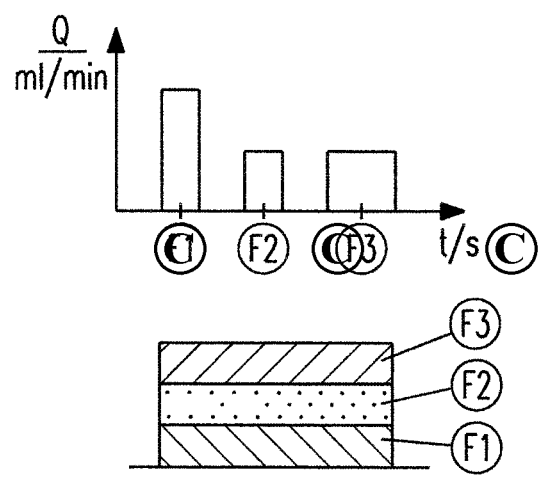
FIG. 5: shows a time diagram with an exemplary pulse sequence for actuation of the medical device in interval operation.

FIG. 5 shows by way of example a possible series of fluid supply sequences for generating a multi-layer structure of different fluid application layers. It can thus, for example, be provided that a first fluid F1 is initially applied with a high volumetric flow onto a target object. At a time interval to the application of first fluid F1, a second fluid F2 with a relatively smaller volumetric flow can be sprayed via the nozzle according to the invention. First fluid F1 and second fluid F2 can be sprayed in each case over a period of spraying, i.e. a time interval from the start of the spray jet until stopping of the spray jet, which is identical or at least similar. As is apparent in FIG. 5, first fluid F1 is first deposited on the target object. Second fluid F2 is subsequently applied onto first fluid F1. Finally, a third fluid F3 can be deposited onto the laminar structure of first fluid F1 and of second fluid F2 after the termination of the fluid jet of fluid F2. Third fluid F3 can be sprayed, for example, as is apparent in the diagram according to FIG. 5, with a similar or identical volumetric flow via the nozzle as second fluid F2. In contrast to second fluid F2, the spraying period for third fluid F3 can, however, be extended. By setting the different volumetric flows of fluids F1, F2, F3, account can be taken of the different viscosities of fluids F1, F2, F3. In this manner, it is achieved that fluids F1, F2, F3 exit out of the nozzle with the same flow speed despite their different viscosity. It can also be provided that fluids F1, F2, F3 in each case exit out of different channel systems 5 of the nozzle so that a mixing of fluids F1, F2, F3 is first carried out on the target object. The laminar structure according to FIG. 5 is therefore substantially exemplary and at most apparent for a moment. In practice, a mixing of the individual fluids is carried out directly on the target object.

The nozzle described above serves to mix and spray fluids. Fluids can be supplied with identical or different volumetric flows and/or have identical or different viscosity. The term fluid comprises here both liquid and gaseous substances and mixtures thereof. In particular, a two-component adhesive can be mixed and sprayed with the nozzle according to the invention, wherein a gluing of the nozzle channels is avoided by the externally mixing function of the nozzle. Such a two-component adhesive normally has a bonding agent and a hardening agent or cross-linking agent. The hardening agent or cross-linking agent is preferably sprayed as a first fluid via first supply channel 11, first chamber 12 and first outlet channel 10. For example, thrombin can be used as the hardening agent or cross-linking agent. The bonding agent is preferably sprayed as a second fluid via second supply channel 21, second chamber 22 and second outlet channel 20. One preferred bonding agent is, for example, fibrinogen. The bonding agent and the hardening agent or cross-linking agent first come into contact with one another in overlapping region 34 so that the cross-linking reaction or curing takes place outside the nozzle. Within the nozzle, the first fluid and the second fluid, in particular the bonding agent and the hardening agent or cross-linking agent, are guided entirely separately from one another.

In addition, a substance which has, for example, biological material, in particular cells can be supplied as a third fluid. In order to protect the biological material, it is provided that the third fluid is mixed in largely without deflection, i.e. under the influence of the lowest possible shear forces. This can be performed on one hand as a result of the coaxial arrangement of third supply channel 31 to mixing chamber 22*b* according to FIG. 1 and on the other hand as a result of a separate outlet channel 30 in which third supply channel 31 discharges coaxially (FIG. 2). The supply of the third fluid laterally into second outlet channel 20 according to FIG. 3 also protects biological tissue which is mixed in with the third fluid.

It applies to all the exemplary embodiments that the nozzle according to the invention preferably has volumetric flow-adapted cross-sections of inlet openings 13, 23 in order to equalise the different viscosity and/or the different volumetric flows of the individual fluids. It is furthermore possible to provide a different number of inlet openings 13, 23 instead of individual inlet openings of different sizes. First chamber 12 can thus have, for example, a larger number of inlet openings 13 than second chamber 22, or vice versa. Moreover, the cross-sections of outlet channels 10, 20 can be selected as a function of the volumetric flow ratio of the individual fluids in order to set substantially identical average flow speeds of the fluids exiting out of the nozzle. As a result of an inclination of the central axes of outlet channels 10, 20, overlapping region 34 can furthermore be enlarged in order to improve the mixing of the individual fluids. An angle which is greater than 0° and less than 180° preferably exists between the central axes of outlet channels 10, 20.

In the context of the application, a method for mixing at least two fluids by means of an externally mixing nozzle for medical purposes is furthermore disclosed which has at least two outlet channels 10, 20 and at least two inlet openings 13, 23 with different or identical cross-sections, wherein two fluids with different volumetric flows and/or different viscosity are sprayed, and wherein the ratio of the cross-sections of inlet channels 13, 23 and/or outlet channels 10, 20 corresponds to the ratio of the volumetric flows so that the fluids flow with substantially identical average flow speeds through outlet channels 10, 20 and/or inlet openings 13, 23. An externally mixing nozzle, a medical instrument and a medical device for spraying substances, in particular biological material are furthermore described.

LIST OF REFERENCE NUMBERS

5 Channel system
10 First outlet channel
11 First supply channel
11*a* End portion of first supply channel 11
12 First chamber
12*a* First vortex chamber
13 First inlet opening
14 First fluid cone
15 Bottleneck
20 Second outlet channel
21 Second supply channel
21*a* End portion of second supply channel 21
22 Second chamber
22*a* Second vortex chamber
22*b* Mixing chamber
23 Second inlet opening
24 Second fluid cone
30 Third outlet channel
31, 41 Third supply channel
33 Spot jet
34 Overlapping region
40 End surface
41*a* End portion of third supply channel 41

What is claimed is:

1. An apparatus for the supply of substances, the apparatus comprising an externally mixing nozzle comprising:

a first outlet channel and a second outlet channel, which are arranged spaced apart from one another in such a manner that fluid cones exiting from the first and second outlet channels for the mixing of fluids at least partially overlap, wherein the first outlet channel is fluid-connected to a first cylindrical vortex chamber, and the second outlet channel is fluid-connected to a second cylindrical vortex chamber, and a first supply channel is configured to discharge laterally into the first cylindrical vortex chamber, and a second supply channel is configured to discharge laterally into the second cylindrical vortex chamber;

wherein the fluids entering the first and second cylindrical vortex chambers via the respective first and second supply channels are directed transversely with respect to the respective fluids exiting the first and second cylindrical vortex chambers via the respective first and second outlet channels to induce a fluid vortex within each of the first and second cylindrical vortex chambers, wherein at least one third supply channel is provided which discharges a liquid containing biologic material including biological cells for mixing with the fluids supplied by the first and second supply channels, wherein the third supply channel discharges the liquid containing biologic material directly into a third outlet channel that is arranged between the first and second outlet channels such that the liquid containing biologic material is released into the fluid cones exiting from the first and second outlet channels, so that the liquid containing biologic material is subject to lower shear forces than the fluids supplied by the first and second supply channels to protect the biological cells in the liquid, and wherein the first and second cylindrical vortex chambers each have a cross-sectional area in a plane perpendicular to a central axis of the corresponding cylindrical vortex chamber and the first and second supply channels each have a cross-sectional area in a plane perpendicular to a central axis of the corresponding supply channel, and the cross-sectional area of the first cylindrical vortex chamber is greater than the cross-sectional area of the first supply channel, and the cross-sectional area of the second cylindrical vortex chamber is greater than the cross-sectional area of second supply channel.

2. The apparatus according to claim 1, wherein the first vortex chamber and the second vortex chamber are connected in each case to the first or second supply channel via an inlet opening, wherein the inlet opening of the first vortex chamber and the inlet opening of the second vortex chamber have different cross-sectional shapes.

3. The apparatus according to claim 1, wherein at least the first outlet channel and the second outlet channel have longitudinal axes oriented parallel or at an angle to one another.

4. The apparatus according to claim 1, further comprising a medical instrument having the externally mixing nozzle, wherein the instrument is configured to connect to a medical device with a control unit for setting the supply of substances to the first, second, and third supply channels.

5. The apparatus according to claim 4, wherein the first vortex chamber and the second vortex chamber are connected in each case to the first or second supply channel via an inlet opening;
   wherein the control unit is adapted for setting the supply of substances to the first, second, and third supply channels in such a manner that, with different volumetric flows and/or different viscosity of the fluids, said fluids flow with substantially identical flow speeds through the outlet channels and/or the inlet openings.

6. The apparatus according to claim 4, wherein the control unit is adapted for setting the supply of substances to the first, second, and third supply channels in such a manner that the different fluids can be supplied independently of one another in any desired sequence.

7. The apparatus according to claim 1, wherein the first vortex chamber and the second vortex chamber are connected in each case to the first or second supply channel via an inlet opening;
   further comprising a control unit which is adapted for setting the supply of substances to the first, second, and third supply channels in such a manner that, with different volumetric flows and/or different viscosity of the fluids, said fluids flow with substantially identical flow speeds through the outlet channels and/or the inlet openings.

8. The apparatus according to claim 7, wherein the control unit is adapted for setting the supply of substances to the first, second, and third supply channels in such a manner that the different fluids can be supplied independently of one another in any desired sequence.

9. The apparatus according to claim 1, further comprising a control unit which is adapted for setting the supply of substances to the first, second, and third supply channels in such a manner that the different fluids can be supplied independently of one another in any desired sequence.

10. A method for mixing at least two fluids, the method comprising:
   using an externally mixing nozzle, which has at least two outlet channels and at least two inlet openings with different or identical cross-sections, to mix at least two fluids, by:
      conducting a first fluid via a first supply channel laterally into a first cylindrical vortex chamber which is fluid-connected to a first outlet channel,
      conducting a second fluid via a second supply channel laterally into a second cylindrical vortex chamber which is fluid-connected to a second outlet channel which is spaced apart from the first outlet channel, such that the fluids entering the first and second cylindrical vortex chambers via the respective first and second supply channels are directed transversely with respect to the respective fluid exiting the first and second cylindrical vortex chambers via the respective first and second outlet channels to induce a fluid vortex within each of the first and second cylindrical vortex chambers, and
   wherein the first and second cylindrical vortex chambers each have a cross-sectional area in a plane perpendicular to a central axis of the corresponding cylindrical vortex chamber and the first and second supply channels each have a cross-sectional area in a plane perpendicular to a central axis of the corresponding supply channel, and the cross-sectional area of the first cylindrical vortex chamber is greater than the cross-sectional area of the first supply channel, and the cross-sectional area of the second cylindrical vortex chamber is greater than the cross-sectional area of second supply channel,
   flowing the first fluid out via the first outlet channel and the second fluid out via the second outlet channel in such a manner that overlapping fluid cones are formed,
   wherein the first fluid and the second fluid have different volumetric flows and a ratio of the cross-sections of the inlet openings and/or the outlet channels corresponds to a ratio of the volumetric flows so that the first fluid and the second fluid flow with substantially identical average flow speeds through the outlet channels and/or the inlet openings, and
   wherein at least one third supply channel is provided which discharges a liquid containing biologic material including biological cells for mixing with the first and second fluids, wherein the third supply channel discharges the liquid containing biologic material directly into a third outlet channel that is arranged between the first and second outlet channels such that the liquid containing biologic material is released into the fluid cones exiting from the first and second outlet channels, so that the liquid containing biologic material is subject to lower shear forces than the fluids supplied by the first and second supply channels to protect the biological cells in the liquid.

11. The method according to claim 1, further comprising controlling the supply of the first fluid to the first vortex chamber and/or the supply of the second fluid to the second vortex chamber.

12. The method according to claim 1, further comprising conducting a liquid containing biologic material including biological cells via the third outlet channel into the overlapping fluid cones of the first fluid and of the second fluid.

* * * * *